United States Patent
Cai et al.

(10) Patent No.: US 12,320,817 B2
(45) Date of Patent: Jun. 3, 2025

(54) ENZYME-LINKED IMMUNOSORBENT ASSAY (ELISA) METHOD AND MONOCLONAL ANTIBODY FOR GIANT PANDA RELAXIN-3 (RLN3)

(71) Applicant: Chengdu Research Base of Giant Panda Breeding, Chengdu (CN)

(72) Inventors: Kailai Cai, Chengdu (CN); Rong Hou, Chengdu (CN); Yuliang Liu, Chengdu (CN); Jingchao Lan, Chengdu (CN); Mingxi Li, Chengdu (CN); Juan Wang, Chengdu (CN); Mengshi Zhang, Chengdu (CN); Shenfei Wang, Chengdu (CN); Feiping Li, Chengdu (CN); Xianbiao Hu, Chengdu (CN)

(73) Assignee: Chengdu Research Base of Giant Panda Breeding, Chengdu (CN)

( * ) Notice: Subject to any disclaimer, the term of this patent is extended or adjusted under 35 U.S.C. 154(b) by 0 days.

(21) Appl. No.: 18/808,126

(22) Filed: Aug. 19, 2024

(65) Prior Publication Data
US 2025/0067756 A1    Feb. 27, 2025

(30) Foreign Application Priority Data
Aug. 21, 2023 (CN) .......................... 202311051419.5

(51) Int. Cl.
  *G01N 33/74* (2006.01)
  *C07K 16/26* (2006.01)
  *G01N 33/58* (2006.01)

(52) U.S. Cl.
CPC ............. *G01N 33/74* (2013.01); *C07K 16/26* (2013.01); *G01N 33/58* (2013.01); *G01N 2333/64* (2013.01)

(58) Field of Classification Search
None
See application file for complete search history.

(56) References Cited

U.S. PATENT DOCUMENTS

2008/0051336 A1    2/2008    Bonaventure et al.

FOREIGN PATENT DOCUMENTS

| CN | 1633498 A | 6/2005 |
|---|---|---|
| CN | 108823172 A | 11/2018 |
| CN | 114624452 A | 6/2022 |
| CN | 116338212 A | 6/2023 |
| CN | 116375861 A | 7/2023 |
| ES | 2365855 T3 | 10/2011 |

OTHER PUBLICATIONS

Steinetz et al. (2005, Ann. N.Y. Acad. Sci. 1041:367-378).*
Yongyou Feng, et al., Artificial assistance helps red pandas raise quadruplets alive, Sichuan Journal of Zoology, 2022, p. 533, vol. 41 No. 5.
Don R. Bergfelt, et al., Relaxin: A hormonal aid to diagnose pregnancy status in wild mammalian species, Theriogenology, 2014, pp. 1187-1198, vol. 82.
(RLN3) Elisa Kit, X-Y Biotechnology, 2023, retrieved from: https://b2b.baidu.com/land?id=2dc1f3139312a725226f7b1433b4284410.

* cited by examiner

*Primary Examiner* — Elizabeth C. Kemmerer
(74) *Attorney, Agent, or Firm* — Bayramoglu Law Offices LLC

(57) ABSTRACT

An enzyme-linked immunosorbent assay (ELISA) method and a monoclonal antibody for giant panda relaxin-3 (RLN3) are provided. The method includes: conducting ELISA with an anti-giant panda RLN3 monoclonal antibody as a coating antibody and an anti-RLN3 polyclonal antibody as a labeling antibody, where the anti-giant panda RLN3 monoclonal antibody is secreted by a hybridoma cell line RLN-3; and the hybridoma cell line RLN-3 was deposited in the China Center for Type Culture Collection (CCTCC) of Wuhan University, Wuhan, China on Jan. 7, 2021, with an accession number of CCTCC NO: C202129. In addition, an ELISA method for detecting RLN3 in giant panda urine is developed, in which a prepared anti-giant panda RLN3 monoclonal antibody is used as a coating antibody and an anti-giant panda RLN3 polyclonal antibody is used as a labeling antibody. The method can monitor a change in giant panda RLN3 timely by determining giant panda RLN3.

6 Claims, 3 Drawing Sheets
Specification includes a Sequence Listing.

```
                         SEQUENCE LISTING

Sequence total quantity: 6
SEQ ID NO: 1             moltype = AA  length = 114
FEATURE                  Location/Qualifiers
source                   1..114
                         mol_type = protein
                         organism = synthetic construct
SEQUENCE: 1
QVQLKQSGPQ LLRPGASVKI SCKASGYSFT RYWIHWVKQR PGQGLEWIGM IDPSDSESRL    60
NQKFKDKATL TEDKSSSTAY MQLSSPTSED SAVYYCVRRY FDYWGHGTTL TVSS         114

SEQ ID NO: 2             moltype = AA  length = 111
FEATURE                  Location/Qualifiers
source                   1..111
                         mol_type = protein
                         organism = synthetic construct
SEQUENCE: 2
DIVLTQSPAS LAVSLGQRTA ISCKASQSVD YDGDSYMNWY QQKPGQPPNL LIYAASNIES    60
GIPARFSGSG YGTDFTLNIH PVEEEDVATY YCQQSNEDPL TFGAGTKLEL K            111

SEQ ID NO: 3             moltype = AA  length = 139
FEATURE                  Location/Qualifiers
source                   1..139
                         mol_type = protein
                         organism = synthetic construct
SEQUENCE: 3
MAKHPLLLLL TVWVLAGELW LRTEARASPF GVKLCGREFI RAVIFTCGGS RWRRADVLAP    60
EATGDPFPDA DSDTDSELDE AVASSELLAM TKYPLASYGG RPGWQGTPGT LRGGRDVVAG   120
LSSNCCKWGC SKSEISSLC                                               139

SEQ ID NO: 4             moltype = AA  length = 24
FEATURE                  Location/Qualifiers
source                   1..24
                         mol_type = protein
                         organism = synthetic construct
SEQUENCE: 4
DVVAGLSSNC CKWGCSKSEI SSLC                                          24

SEQ ID NO: 5             moltype = AA  length = 139
FEATURE                  Location/Qualifiers
source                   1..139
                         mol_type = protein
                         organism = synthetic construct
SEQUENCE: 5
MAKHPLLLLL TVWVLAGELW LRTEARASPF GVKLCGREFI RAVIFTCGGS RWRRADVLAP    60
EATGDPFPDA DSDTDSELDE AVASSELLAM TKYPLASYGG RPGWQGTPGT LRGGRDVVAG   120
LSSNCCKWGC SKSEISSLC                                               139

SEQ ID NO: 6             moltype = AA  length = 114
FEATURE                  Location/Qualifiers
source                   1..114
                         mol_type = protein
                         organism = synthetic construct
SEQUENCE: 6
RASPFGVKLC GREFIRAVIF TCGGSRWRRA DVLAPEATGD PFPDADSDTD SELDEAVASS    60
ELLAMTKYPL ASYGGRPGWQ GTPGTLRGGR DVVAGLSSNC CKWGCSKSEI SSLC         114
```

ENZYME-LINKED IMMUNOSORBENT ASSAY (ELISA) METHOD AND MONOCLONAL ANTIBODY FOR GIANT PANDA RELAXIN-3 (RLN3)

CROSS REFERENCE TO THE RELATED APPLICATIONS

This application is based upon and claims priority to Chinese Patent Application No. 202311051419.5, filed on Aug. 21, 2023, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBCD166-PKG_Sequence_Listing.xml, created on 08/09/2024, and is 6,754 bytes in size.

TECHNICAL FIELD

The present disclosure belongs to the field of enzyme-linked immunosorbent assay (ELISA) methods, and specifically provides a monoclonal antibody, a kit, and an ELISA method for giant panda relaxin-3 (RLN3) to monitor a change in RLN3 timely.

BACKGROUND

Relaxin (RLN) is a short-cycle polypeptide hormone found and named as a gonadal hormone in gophers and guinea pigs. RLN plays an important role in pregnancy, childbirth, and other aspects of female reproduction. RLN and analogues thereof have been used as therapeutic drugs for some diseases in clinical practice and livestock production. RLN and analogues thereof are expected to serve as indicators for the prediction and evaluation of some diseases in the future, which is of great significance for the development and utilization of novel drugs.

Studies have shown that RLN can promote the growth and softening of reproductive tracts in female animals during a pregnancy, and in rats, RLN can inhibit the apoptosis of cells, promote the accumulation of epithelial cells and stromal cells, stimulate the proliferation of cells, and cause a change in the extensibility of the cervix and vagina. The injection of RLN into mammals can significantly reduce the frequency and amplitude of myometrial contractions. The stimulation of estrogen and progesterone can increase the sensitivity of the myometrium in rats and pigs to RLN. Further studies have shown that RLN may reduce the spontaneous contractions of uteri in pregnant animals through a synergistic effect of estrogen and progesterone. Therefore, the detection of an RLN level in vivo is of important guiding significance for reproduction.

Studies have shown that dog RLN detection can identify a pregnancy or assess the viability of a fetus, but there may be a false-positive result after abortion. RLN3, as one of the important members of the RLN family, can be used to assess an RLN level in vivo. However, there is currently a lack of a method for detecting an RLN level in a giant panda, and the changes in RLN levels in giant pandas still need to be investigated. In conclusion, the establishment of a method for detecting RLN3 to monitor a change in RLN3 timely and reflect an RLN level in a giant panda timely is of great significance for monitoring the reproduction of giant pandas.

SUMMARY

In order to solve the above problems, the present disclosure provides a specific anti-giant panda RLN3 monoclonal antibody and polyclonal antibody, and develops a method for detecting RLN3 in giant panda urine with these two antibodies as a coating antibody and a labeling antibody and a giant panda RLN3 recombinant protein to monitor a change in RLN3 timely.

To allow the above objective, the present disclosure adopts the following technical solutions:

An ELISA method for RLN3 is provided, including: conducting ELISA with an anti-giant panda RLN3 monoclonal antibody produced by a hybridoma cell line RLN-3 as a coating antibody and an anti-RLN3 polyclonal antibody as a labeling antibody.

The hybridoma cell line RLN-3 was deposited in the China Center for Type Culture Collection (CCTCC) of Wuhan University, Wuhan, China on Jan. 7, 2021, with an accession number of CCTCC NO: C202129.

Further, when the RLN3 is detected, the ELISA is conducted with the anti-giant panda RLN3 monoclonal antibody produced by the hybridoma cell line RLN-3 as a primary coating antibody and the anti-RLN3 polyclonal antibody as the labeling antibody.

Further, the anti-giant panda RLN3 monoclonal antibody includes an RLN3-specific sequence (RLN3-2) with an amino acid sequence shown in SEQ ID NO: 4 as an immunogen, and is secreted by the hybridoma cell line RLN-3.

Further, a preparation method of the anti-giant panda RLN3 monoclonal antibody is as follows:
  (1) designing an RLN3-specific sequence with an amino acid sequence shown in SEQ ID NO: 4, and conjugating the RLN3-specific sequence to keyhole limpet hemocyanin (KLH) to produce an immunogen RLN3-2-KLH;
  (2) immunizing mice with the immunogen RLN3-2-KLH;
  (3) isolating an anti-giant panda RLN3 monoclonal antibody-secreting hybridoma cell line RLN-3; and
  (4) subjecting the hybridoma cell line RLN-3 to expanded cultivation to obtain the anti-giant panda RLN3 monoclonal antibody.

Further, a preparation method of the anti-RLN3 polyclonal antibody is as follows:
  (1) preparation of an immunogen and standard: chemically synthesizing a gene fragment of a partial coding region of RLN3, enzyme cleavage sites NdeI and HindIII, and a stop codon, forward inserting the gene fragment, the enzyme cleavage sites, and the stop codon into a pET30a vector to obtain a recombinant vector, and identifying the recombinant vector through enzyme cleavage with NdeI-HindIII; and expressing a recombinant protein (RLN3) with a 6*His-tagged RLN3 26-139 amino acid fragment by a prokaryotic expression system, and purifying the recombinant protein through affinity chromatography (Ni-IDA resin) to obtain a purified protein as the immunogen for developing the anti-RLN3 polyclonal antibody and a standard for ELISA; and
  (2) preparation of the anti-RLN3 polyclonal antibody: immunizing a rabbit with the immunogen recombinant protein (RLN3) obtained in the step (1), collecting cardiac blood from an immunized rabbit, and isolating serum from the cardiac blood; and subjecting isolated serum to affinity chromatography, collecting a high-concentration purified product step by step, and concentrating the purified product by an ultrafiltration centrifuge tube to obtain a concentrated anti-RLN3 polyclonal antibody.

Further, the immunizing a rabbit with the immunogen in the step (2) includes: mixing 500 g of the immunogen with an equal volume of a Freund's complete adjuvant thoroughly to obtain an initial immunization reagent, and injecting the rabbit with the initial immunization reagent for initial immunization; two weeks later, mixing 250 g of a conjugated immunogen with an equal volume of a Freund's incomplete adjuvant thoroughly to obtain a first booster immunization reagent, and injecting the rabbit with the first booster immunization reagent for first booster immunization; one week later, conducting second booster immunization with the same immunizing dose and method as the first booster immunization; and when a serum titer of an ear vein of the rabbit reaches 1:10,000, conducting third booster immunization with the same immunizing dose and method as the first booster immunization.

Further, in the step (2), the cardiac blood is collected three days after the third booster immunization.

Further, a packing for the affinity chromatography in the step (2) is protein G-agarose.

Further, ELISA is adopted for detection.

Further, during the detection, anti-RLN3 antibodies include a monoclonal antibody and a polyclonal antibody.

Further, the following contents are included: a 96-well microplate coated with the first anti-giant panda RLN3 monoclonal antibody, the second anti-RLN3 polyclonal antibody labeled with biotin, a streptavidin-horseradish peroxidase (lRP) complex, a standard, a sample buffer, a wash buffer, a chromogen substrate solution, and a chromogen stop solution.

Further, the standard is the recombinant protein RLN3.

Further, the chromogen substrate solution is a 3,3',5,5'-tetramethylbenzidine (TMB) chromogenic solution, and the chromogen stop solution is a sulfuric acid solution with a concentration of 1 M.

The present disclosure has the following beneficial effects:

With an anti-giant panda RLN3 monoclonal antibody as a coating antibody and an anti-giant panda RLN3 polyclonal antibody as a labeling antibody, the present disclosure develops an ELISA method for detecting RLN3 in giant panda urine. The method can monitor a change in giant panda RLN3 timely by determining giant panda RLN3.

DETAILED DESCRIPTION OF THE EMBODIMENTS

Figure 1:
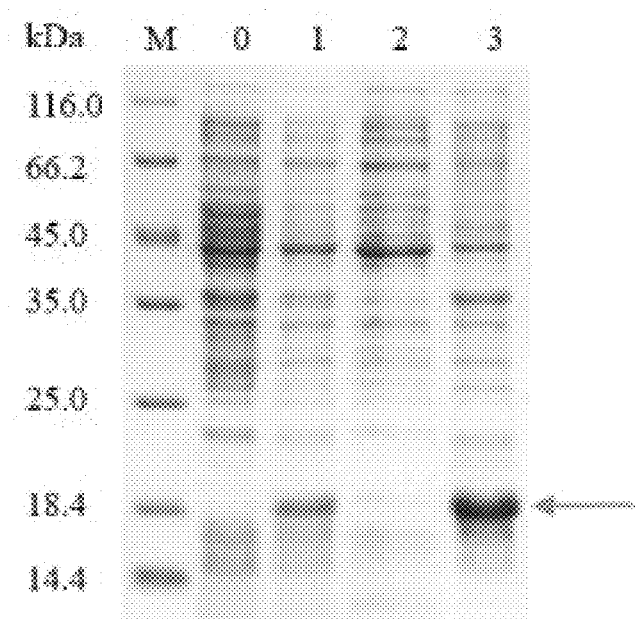
FIG. 1 shows the expression results of an RLN3 protein in BL21 (DE3) according to sodium dodecyl sulfate-polyacrylamide gel electrophoresis (SDS-PAGE) analysis, where a band M: SDS-PAGE Protein Marker; a band 0: control (without isopropyl-β-D-thiogalactoside (IPTG)); a band 1: induction at 37° C. for 16 h; a band 2: a supernatant obtained after whole-bacterium disruption; and a band 3: a precipitate obtained after whole-bacterium disruption.

Specific implementations of the present disclosure are described below to facilitate those skilled in the art to understand the present disclosure, but it should be known that the present disclosure is not limited to the scope of the specific implementations. For those of ordinary skill in the art, as long as various changes are within the spirit and scope of the present disclosure that are defined and determined by the attached claims, these changes are obvious, and all innovations using the concept of the present disclosure are protected.

The experimental methods used in the following examples are conventional unless otherwise specified. The materials, reagents, or the like used in the following examples are commercially available unless otherwise specified.

Example 1

Preparation of an Anti-Giant Panda RLN3 Monoclonal Antibody

1. Design and synthesis of a specific polypeptide fragment: According to the RLN3 amino acid sequence with an accession number: XP_002921067.1: MAKHPLLLLLTVWVLAGELWLRTEAR-ASPFGVKLCGREFIRAVIFTCGGSRWRRADVLA PEATGDPFPDADSDTDSELDEAVASSELLAMT-KYPLASYGGRPGWQGTPGTLRGGRDVV AGLSSNCCKWGCSKSEISSLC (SEQ ID NO: 3) in the NCBI database and with reference to the sequence analysis of other species, an RLN3-specific sequence DVVAGLSSNCCKWGCSKSEISSLC (RLN3-2) (SEQ ID NO: 4) was designed, artificially synthesized, and conjugated to KLH to obtain an immunogen (RLN3-2-KLH) for producing a specific antibody. A synthesis process of the polypeptide fragment is relatively mature. With the sequences disclosed in the present application, the Sangon Biotech (Shanghai) Co., Ltd. can produce the polypeptide fragment RLN3-2 and the immunogen RLN3-2-KLH.

2. Immunization of mice with the antigen: A mixture of an adjuvant and the antigen in 1:1 was adopted for immunization (when an amount of the antigen was insufficient, the antigen could be first mixed with sodium chloride and then subjected to emulsification with the adjuvant). A Freund's complete adjuvant was adopted for initial immunization, and a Freund's incomplete adjuvant was adopted for subsequent immunization. Sterilized syringes, three-way pipes, and disposable syringes were prepared before immunization. The antigen and NaCl (400 L in total, an amount for four mice) were drawn into a sterilized syringe, and the adjuvant (400 L in total, an amount for four mice) was drawn into a sterilized syringe. Finally, the sterilized syringes were connected to a three-way pipe for emulsification (the emulsification was conducted for about 10 min until a water-in-oil state was reached) to obtain an emulsified mixture, and the emulsified mixture was transferred into a disposable syringe for injection.

Day 1: intraperitoneal injection, 200 μL/mouse (antigen dose: 100 μg/mouse);

day 14: intraperitoneal injection, 200 μL/mouse (subsequent antigen dose: 50 μg/mouse);

day 21: intraperitoneal injection, 200 μL/mouse; and day 27: intraperitoneal injection, 200 μL/mouse.

3 to 4 days after the third immunization, blood was collected from a tail of each mouse and centrifuged at 12,000 rmp for 8 min to obtain serum, and the serum was collected and tested for a titer. A microplate was coated with TSH-1 as an antigen at a concentration of 2 μg/mL, and a serum titer was detected by ELISA. After a titer was qualified, it was ready to conduct fusion. If the titer was insufficient, the immunization was continued until the titer was qualified. Immunized serum titers were shown in Table 1.

TABLE 1

Serum titers after immunization

| Serum dilution ratio | Serum titers in immunized mice |
|---|---|
| 1:100 | 3.337 |
| 1:500 | 3.271 |
| 1:2000 | 2.889 |
| 1:5000 | 2.568 |
| 1:10000 | 1.985 |
| 1:20000 | 1.457 |
| 1:40000 | 0.884 |
| Negative control | 0.068 |

The above results indicated that the mice met the immunization requirements and it was ready to conduct a cell fusion experiment.

3. Cell fusion:

3.1 Recovery of myeloma cells (SP2): Cryopreserved cells were taken out from liquid nitrogen, immediately placed in a 37° C. water bath for thawing to make the cells loosened, and then transferred into a 15 mL centrifuge tube. About 5 mL of PBS was added to the centrifuge tube, thorough mixing was conducted, and the centrifuge tube was centrifuged at 1,000 rpm for 5 min to obtain a supernatant and an SP2 cell pellet. The supernatant was discarded. The SP2 cell pellet was washed twice, inoculated into a culture flask marked, and finally cultivated in a 37° C. and 5% $CO_2$ incubator.

3.2 Passage of SP2 cells: When cells at a bottom of the culture flask grew to a confluency of about 80%, the cells could be passaged. The cells were removed from a wall through pipetting up and down to obtain a cell suspension, the cell suspension was pipetted into a 15 mL centrifuge tube and centrifuged at 1,000 r/min for 5 min to obtain a supernatant, and the supernatant was discarded. 5 mL of PBS was added to the centrifuge tube to obtain a mixture, the mixture was pipetted up and down for thorough mixing and then centrifuged to obtain a supernatant, and the supernatant was discarded. The PBS-washing step was repeated 2 times. Cells obtained after washing were suspended with 2 mL of a 10% complete medium, and an appropriate amount of the cells was inoculated into a culture flask and cultivated in a carbon dioxide incubator.

3.3 Preparation of trophoblast macrophages (which could be prepared the day before fusion):

A mouse was sacrificed through cervical dislocation. During the cervical dislocation, the compression to an abdominal cavity should be minimized as much as possible to prevent blood vessels in the abdominal cavity from being damaged, thereby avoiding a large number of blood cells in feeder cells. The mouse was soaked in 75% alcohol for 5 min, and then a tail of the mouse was held to make the mouse move up and down in alcohol several times for rinsing. The mouse was placed in a sterile petri dish. The skin was cut with sterile scissors from the post abdomen and skin parts at two sides were separated by hands to expose the abdomen, where a peritoneum should not be damaged. The peritoneum was wiped with an alcohol cotton ball. 6 mL to 8 mL of an incomplete medium including penicillin-streptomycin was drawn with a syringe and injected into the abdominal cavity (penicillin-streptomycin: incomplete medium=1:100). When the peritoneum was lifted with forceps during injection, a syringe needle should be prevented from piercing organs such as an intestine in the abdominal cavity. The abdomen was gently massaged with a cotton ball for 1 min, then the injected medium was drawn out, transferred into a centrifuge tube, and centrifuged at 1,000 r/min for 5 min to obtain a supernatant, and the supernatant was discarded. Washing was conducted with PBS four times. Cells were suspended in a 10% complete medium to obtain a cell suspension.

The cell suspension was added to a 96-well plate at 100 μL/well, and the 96-well plate was incubated in a $CO_2$ incubator (there should not be too many macrophages, and a part of the collected cells can be discarded according to an actual situation).

3.4 Preparation of immune splenocytes:

(1) Collection of a Mouse Spleen

A mouse meeting the immunization requirements was taken. An aseptic operation was required to prevent cell contamination. After being sacrificed, the mouse was soaked in 75% alcohol for about 5 min, placed in a sterile petri dish, and arranged at a position conducive to the operation (in a clean bench) for dissection. A small cut was created with scissors at a tail of the mouse, then a fur layer was split by hands, and an exposed part was gently wiped with an alcohol cotton ball. Then a translucent membrane wrapping internal organs was lifted with forceps and cut to expose the spleen, the spleen was gently taken out with fat tissues on the spleen removed as much as possible, and the collected spleen was washed in PBS.

(2) Preparation of a Splenocyte Suspension

The spleen was rinsed with PBS about 3 times, then placed in a petri dish, and cut with scissors into pieces as small as possible, PBS was added the petri dish for washing, and filtration was conducted to obtain a tissue precipitate and a splenocyte suspension. The tissue precipitate was discarded. The splenocyte suspension was centrifuged at 1,000 r/min for 5 min to obtain a supernatant and a cell pellet, and the supernatant was discarded. 5 mL of PBS was added to the cell pellet for washing, and centrifugation was conducted at 1,000 r/min for 5 min. The washing step was repeated three times. Cells obtained after washing were suspended with 2 mL of an incomplete medium (DMEM) and diluted 100-fold or 1000-fold for cell counting, and the remaining cells were placed in a 37° C. water bath for later use.

(3) Preparation of an SP2 cell suspension: A culture was drawn with a dropper to blow a film at a bottom of a culture flask (cells were suspended or slightly adherent to a wall). Then the culture was transferred by a pipette to a 15 mL centrifuge tube and centrifuged at 1,000 r/min for 5 min to obtain a supernatant. The supernatant was discarded. 5 mL of PBS was added to the centrifuge tube, thorough mixing was conducted, and the centrifuge tube was centrifuged at 1,000 r/min for 5 min. The washing step was repeated twice. Cells obtained after washing were suspended with 2 mL of an incomplete medium (DMEM) and diluted 100-fold or 1000-fold for cell counting, and the remaining cells were placed in a 37° C. water bath for later use.

3.5 Cell Fusion Under an Action of PEG

SP2 and splenocytes were mixed in a ratio of 1:4 (between 1:10 and 1:4) and centrifuged at 600 rpm for 3 min to obtain a supernatant, and the supernatant was discarded. A bottom of a centrifuge tube was gently flicked to make a cell pellet loosened slightly. 0.6 mL of a 50% PEG solution pre-warmed at 37° C. was slowly added to the centrifuge tube within 1 min during which the centrifuge tube was shaken and tapped slightly, and the centrifuge tube was allowed to stand for 1 min. 10 mL of an incomplete medium pre-warmed at 37° C. was added dropwise at a constant speed to the centrifuge tube to stop the action of PEG, during which the centrifuge tube was tapped and rotated. Then the centrifuge tube was allowed to stand for 2 min and centrifuged at 800 rpm for 5 min to obtain a supernatant and a cell pellet, and the supernatant was discarded. The cell pellet was washed twice with PBS or an incomplete medium to remove PEG.

After washing, the supernatant was abandoned and the cells were suspended with 10 mL of an HAT selective medium. The cells were inoculated at 100 µL/well into a 96-well plate with a feeder cell layer (which was the macrophage plate prepared previously, where a liquid in each well was removed and then an incomplete medium was added for washing and then removed), and the plate was incubated in a $CO_2$ incubator for 4 h. Then an HAT-containing complete medium (19.6 mL of a 10% complete medium+0.4 mL of HAT) was added to each well at 100 µL/well, and the plate was incubated in a $CO_2$ incubator.

3.6 Selective Cultivation (1) On day 4 of fusion cultivation, a half-HAT medium change was conducted as follows: 100 µL of a supernatant in each well of the 96-well plate was removed by a pipette, and then 100 µL of a fresh HAT medium was added to each well (the HAT medium was prepared as follows: 10% complete medium: HAT=1:50). That is, the HAT medium required by each plate was obtained by adding 200 µL of 50×HAT to 10 mL of a complete medium.

(2) On day 7 of fusion cultivation, a half-HT medium change was conducted as follows: 100 µL of a supernatant in each well of the 96-well plate was removed by a pipette, and then 100 µL of a fresh HT medium was added to each well (the HT medium was prepared as follows: 10% complete medium: HT=1:50). That is, the HT medium required by each plate was obtained by adding 200 µL of 50×HT to 10 mL of a complete medium.

3.7 Positive Clone Screening

On about day 7 of cultivation, obvious clone cells could be seen in each well, and when enough clone cells grew (on about day 12), a culture could be collected and tested to determine whether an antibody was secreted.

(1) A corresponding ELISA plate coated previously (which was coated with TSH-1 at a concentration of 2 µg/mL) was taken out from a refrigerator and equilibrated to room temperature, and then a culture to be tested was added to the plate at 100 µL/well. Two wells were adopted as positive and negative controls, where a 10% medium was added for the negative control and serum diluted 10,000-fold (serum of blood collected from the orbit of a mouse before fusion) was added for the positive control.

(2) Incubation: The plate was sealed with a sealing film and then incubated in a 37° C. incubator for 1 h.

(3) Washing: The sealing film was carefully removed, the plate was washed 4 times, and finally the water was removed as much as possible.

(4) Penicillin-streptomycin addition: Penicillin-streptomycin was diluted 10,000-fold and added at 50 µL/well.

(5) Incubation: The plate was sealed with a sealing film and then incubated at 37° C. for 30 min.

(6) Washing: The sealing film was carefully removed, the plate was washed 4 times, and finally the water was removed as much as possible.

(7) Color development: 100 µL of a chromogenic reagent TMB was added to each well, and the plate was gently shaken for thorough mixing and then incubated in an incubator to allow the color development for about 10 min.

(8) Colorimetric assay: A stop solution was added at 50 µL/well (the stop solution was obtained by diluting 21.5 mL of concentrated sulfuric acid to 200 mL), and the plate was gently shaken for thorough mixing. A wavelength of a microplate reader was set to 450 nm, and each well was tested by the microplate reader.

A well with a high positive result (which was at least 4 times a result of the negative control) was selected as a positive clone well.

3.8 Screening of an Anti-Giant Panda RLN3 Monoclonal Antibody-Secreting Hybridoma Cell Line by a Limiting Dilution Method (1) Counting of cells in the positive well: The screened positive clone well was subjected to limiting dilution. Cells in the well were transferred to a 15 mL centrifuge tube (during which blowing and rotating were conducted to make the cells suspended), and then a 10% complete medium was added to 2 mL. Then counting was conducted by a counting board. Then, a cell suspension with only 1,000 cells was taken for the next experiment (since only one cell was required by each well, about 100 cells were required by one 96-well plate, and 1,000 cells were required by 10 plates).

(2) The cell suspension and 200 mL of a complete medium were thoroughly mixed and then added to ten 96-well plates at 200 µL/well.

(3) The plates were incubated in a $CO_2$ incubator.

(4) After 4 days to 5 days of cultivation, small cell clones could be seen under an inverted microscope, the growth of cells was observed, and wells in which single cells grew and aggregated were recorded.

(5) On day 5 of cultivation, the wells in which single cells grew and aggregated that had been recorded were subjected to a medium change, where a 10% complete medium was added at 100 µL/well.

(6) On day 8 to day 9, cell clones could be seen by naked eyes, and antibody detection was conducted timely. Cultures in wells in which single cells grew and aggregated and wells with cells in a prominent growth state were detected (ELSIA). In a well with a high positive value, the anti-giant panda RLN3 monoclonal antibody-secreting hybridoma cell line grew. In the present disclosure, an anti-giant panda RLN3 monoclonal antibody-secreting hybridoma cell line RLN-3 was finally obtained, which was deposited in the China Center for Type Culture Collection (CCTCC) of Wuhan University, Wuhan, China on Jan. 7, 2021, with an accession number of CCTCC NO: C202129.

3.8 Subtype Identification

The subtype identification was conducted with a Pierce Rapid ELISA Mouse mAb Isotyping Kit 37503.

Preparation: TBS in the kit was dissolved in 500 mL of double distilled water for diluting a sample. 870 mL of double distilled water and 30 mL of 30× Wash Buffer were thoroughly mixed for washing plates. A required number of plates determined according to a quantity of samples were taken, and the remaining plates were put back in a 4° C. freezer and stored. 450 µL of a sample diluent was prepared. 20 µL of a cell culture was pipetted and thoroughly mixed with 980 µL of TBS.

Experimental steps: The plates were equilibrated to room temperature. A sample to be tested was added to each well at 50 µL/well, where 8 wells were set for each sample. Goat Anti-Mouse IgG+IgA+IgM HRP were added at 50 µL/well. The plates were gently shaken for thorough mixing, then sealed with a sealing film, incubated at room temperature for 1 h, and washed 4 times, and the water was removed as much as possible. A TMB chromogenic solution was added at 75 µL/well to allow color development for 5 min to 15 min during which a liquid in each well turned blue. Then a stop solution was added at 75 µL/well to terminate the reaction. It was identified that an antibody secreted by the anti-giant panda RLN3 monoclonal antibody-secreting hybridoma cell line RLN-3 screened had a subtype of IgGl. Results were shown in Table 2.

TABLE 2

Subtypes of hybridoma cell lines

| Subtype | RLN-3 |
| --- | --- |
| IgG1 | 1.0928 |
| IgG2a | 0.0707 |
| IgG2b | 0.0592 |
| IgG3 | 0.0534 |
| IgA | 0.0465 |
| IgGM | 0.0425 |
| Kappa | 1.5175 |
| Lamba | 0.0465 |

3.9 Expanded Cultivation, Purification, and Concentration of the Monoclonal Antibody (1) Batch cultivation: Cells secreting an antibody identified as the monoclonal antibody by subtype identification were transferred to a 24-well plate (during which rotating and blowing were conducted to make the cells suspended and complete transfer was conducted), 600 µL of a 10% complete medium was added, and the cells were cultivated.

(2) The growth of cells was observed, and when enough cells grew, a titer was determined. Cells with a high titer were transferred into a small culture flask and cultivated (cells in the 24-well plate were pipetted up and down to make the cells suspended and then transferred by a pipette to the culture flask, and 7 mL of a 10% complete medium was added).

(3) The growth of cells was observed, and when enough cells grew, the cells were transferred into a large culture flask and cultivated. Cells in one small culture flask were transferred into two large culture flasks and cultivated (cell passage).

(4) The cells could be passaged into a plurality of culture flasks. A part of the cells could be cryopreserved. A culture supernatant could be collected and allowed to pass through a column for antibody purification. A packing used for the column was Pierce Protein G Agarose. A purified anti-giant panda RLN3 monoclonal antibody was concentrated with a 10,000 kda ultrafiltration tube and then stored at −20° C. for later use.

3.10 Cryopreservation of the Monoclonal Antibody-Secreting Cell Line

After the cultivation of the identified anti-giant panda RLN3 monoclonal antibody-secreting hybridoma cell line RLN-3 was stabilized, cells in a culture flask were pipetted up and down to make the cells suspended in a medium (the cells were generally suspended in the medium or grew adherently), then transferred to a 15 mL centrifuge tube, and centrifuged at 1,000 rpm for 5 min. Washing was conducted twice with PBS: A supernatant in the centrifuge tube was discarded, PBS was added to the centrifuge tube, thorough mixing was conducted, and the centrifuge tube was centrifuged at 1,000 rpm for 5 min. The above washing process was repeated. A supernatant was discarded by a pipette, an appropriate amount of a cryopreservation solution (the cryopreservation solution was prepared as follows: 5 mL of serum, 4 mL of DMEM, and 1 mL of DMSO were mixed, inverted up and down for thorough mixing, and filtered for later use) was added to cells, and thorough mixing was conducted to obtain a cell solution. The cell solution was added to cryopreservation tubes at 1 mL/tube. The cell line TSHB-B was placed in a cryopreservation box, placed at −80° C. overnight, and then subjected to long-term storage in liquid nitrogen for later use.

Example 2 Titer determination and sequence determination for the anti-giant panda RLN3 monoclonal antibody A titer of a purified monoclonal antibody obtained from a culture supernatant of the cell line RLN-3 was detected by indirect ELISA, and specific steps were as follows:

(1) A microplate was coated with a 2 µg/mL solution of the polypeptide fragment RLN3-2 in Example 1 at 50 µL/well and incubated at 4° C. overnight.

(2) A coated plate was washed, and then 2% BSA-containing PBS was added at 200 µL/well to block at 37° C. for 2 h.

(3) The plate was washed, then the anti-giant panda RLN3 monoclonal antibody was added at serially-diluted concentrations (1,000-fold, 2,000-fold, 4,000-fold, 8,000-fold, 16,000-fold, 32,000-fold, 64,000-fold, 128,000-fold, 256,000-fold, and 512,000-fold), and PBS was added as a control. The plate was incubated at 37° C. for 1 h.

(4) The plate was washed, an HRP-labeled goat anti-mouse antibody was added at 1:5,000, and the plate was incubated at 37° C. for 1 h.

(5) A TMB chromogenic substrate was added at 100 µL/well to allow a reaction for 5 min.

(6) A stop solution was added at 50 µL/well to stop the reaction.

(7) An OD value of each well at 450 nm was read on a microplate reader. Detection results were shown in Table 3.

As shown in Table 3, a titer of a purified RLN3 antibody from a culture supernatant was $10^6$ or more, indicating that the antibody had a high titer.

TABLE 3

| Antibody titers | |
| --- | --- |
| Antibody dilution factor | OD$_{450}$ |
| 1:1000 | 2.893 |
| 1:2000 | 2.711 |
| 1:4000 | 2.237 |
| 1:8000 | 1.913 |
| 1:16000 | 1.525 |
| 1:32000 | 1.224 |
| 1:64000 | 1.007 |
| 1:128000 | 0.848 |
| 1:256000 | 0.637 |
| 1:512000 | 0.499 |
| Blank control | 0.068 |

The cell line secreting the anti-giant panda RLN3 monoclonal antibody (RLN-3) was sent to GENERAL BIOL (Anhui) for sequencing. A sequence of a heavy-chain variable region of the monoclonal antibody was as follows:

```
                                                (SEQ ID NO: 1)
QVQLKQSGPQLLRPGASVKISCKASGYSFTRYWIHWVKQRPGQGLEWIG

MIDPSDSESRLNQKFKDKATLTEDKSSSTAYMQLSSPTSEDSAVYYCVR

RYFDYWGHGTTLTVSS.
```

A sequence of a light-chain variable region was as follows:

```
                                                (SEQ ID NO: 2)
DIVLTQSPASLAVSLGQRTAISCKASQSVDYDGDSYMNWYQQKPGQPPN

LLIYAASNIESGIPARFSGSGYGTDFTLNIHPVEEEDVATYYCQQSNED

PLTFGAGTKLELK.
```

Example 3

Preparation of an Anti-RLN3 Polyclonal Antibody

1. Preparation of an Immunogen and Standard (1) Construction of an RLN3 Recombinant Plasmid According to an RLN3 amino acid sequence (XP_002921067.1): MAKHPLLLLLTVWV-LAGELWLRTEARASPFGVKLCGRE-FIRAVIFTCGGSRWRRADVLA PEATGDPFP-DADSDTDSELDEAVASSELLAMTKYPLASYGGRP GWQGTPGTLRGGRDVV AGLSSNCCKWGCSK-SEISSLC (SEQ ID NO: 5), gene sequences expressing enzyme cleavage sites NdeI and HindIII, 6*His, and the RLN 26-139 amino acid target fragment: RASPFGVKLCGREFIRAVIFTCGGSRWRRADVLA-PEATGDPFPDADSDTDSELDEAVASSE LLAMTKY-PLASYGGRPGWQGTPGTLRGGRDVVAGLSSNCCK-WGCSKSEISSLC (SEQ ID NO: 6) and a stop codon were synthesized and forward inserted into a pET30a vector to obtain an RLN3 recombinant plasmid named pET30a-RLN3.

(2) Prokaryotic Expression of an RLN3 Recombinant Protein:

The constructed pET30a-RLN3 plasmid was transformed into BL21 (DE3) competent cells, transformed competent cells were then evenly coated on an LB plate (including 50 μg/mL of kanamycin sulfate), and then the LB plate was invertedly incubated in a 37° C. incubator overnight. Monoclones were picked from the plate, inoculated into 4 mL of an LB medium (including 50 μg/mL of kanamycin sulfate), and cultivated until OD$_{600}$ was 0.5 to 0.8. IPTG was added with a final concentration of 0.5 mM, and induced expression was allowed at 37° C. A culture produced after the induction was collected and centrifuged at 12,000 rpm for 5 min to obtain a supernatant and a cell pellet, and the supernatant was discarded. The cell pellet was suspended with PBS, an SDS-PAGE loading buffer was added to obtain a sample, the sample was heated at 100° C. for 10 min and then centrifuged to obtain a supernatant, and then the supernatant was collected for electrophoresis. The electrophoresis was conducted at a steady voltage of 160 V until a bromophenol blue band migrated to a position 1 cm away from a bottom of a gel, and the gel was taken out and stained and destained with a rapid protein gel treatment system. SDS-PAGE analysis results of the induced expression were shown in FIG. 1. According to ultrasonic lysis analysis of whole bacteria, the recombinant protein pET30a-RLN3 was expressed in inclusion bodies.

Figure 2:
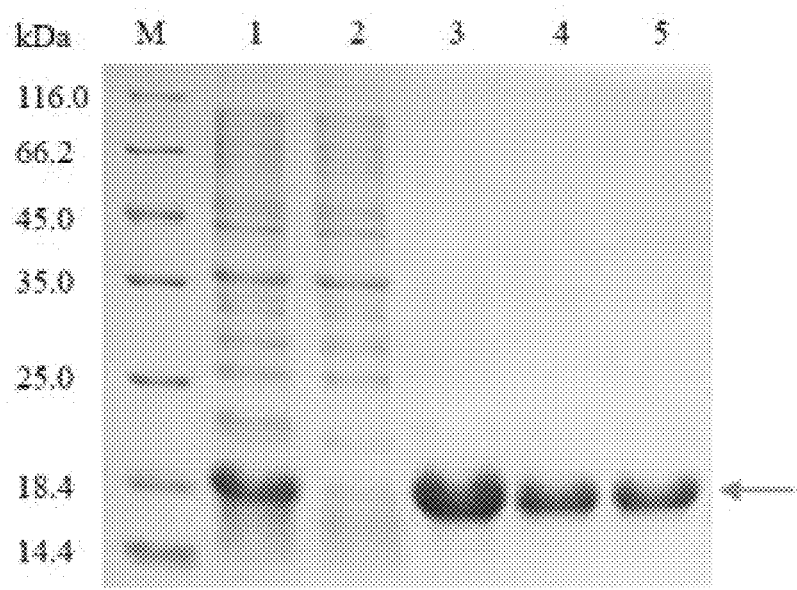
FIG. 2 shows the purification results of an RLN3 protein in inclusion bodies according to SDS-PAGE analysis, where a band M: SDS-PAGE Protein Marker; a band 1: a supernatant obtained after inclusion body lysis and centrifugation; a band 2: an effluent obtained after the supernatant is incubated with Ni-IDA; a band 3: an eluate component of 50 mM imidazole; and bands 4 and 5: eluate components of 300 mM imidazole.

(3) Purification of the RLN3 Recombinant Protein:

The inclusion bodies were washed with 20 mM Tris (pH 8.0), 300 mM NaCl, 1% Triton X-100, 2 mM EDTA, and 5 mM DTT, and then a buffer including 20 mM Tris (pH 8.0), 300 mM NaCl, 8 M Urea, and 20 mM imidazole was used to lyse the inclusion bodies and equilibrate an Ni-IDA column. The target protein was eluted with equilibration buffers including imidazole at different concentrations. Each eluate component was collected and subjected to SDS-PAGE analysis. Analysis results were shown in FIG. 2. Lanes 3 to 5 with relatively-high purities were collected through Ni-IDA affinity chromatography, added to a treated dialysis bag, and dialyzed into a buffer [50 mM Tris (pH 8.8), 300 mM NaCl, 4 mM GSH, 0.4 mM GSSG, 0.4 M L-Arginine, 1 M Urea, and 10% Glycerol] at 4° C. for renaturation, and the renaturated TSHB protein was finally dialyzed into a storage solution including 50 mM Tris (pH 8.8), 300 mM NaCl, and 10% Glycerol for about 6 h to 8 h. After the dialysis and renaturation was completed, a supernatant was filtered through a 0.22 m filter, dispensed, and frozen at −80° C.

(4) Animal Immunization

A specific immunization method for New Zealand white rabbits was as follows: With the prepared pET30a-RLN3 as an antigen, the New Zealand white rabbits (2 kg to 2.5 kg) were immunized subcutaneously. A dose for first immunization was 300 g/rabbit, and a dose for second, third, and fourth immunization was 150 g/rabbit. The immunization was conducted once every 2 to 3 weeks. After the 4 times of immunization, blood was collected and tested by indirect ELISA to determine a titer of an antiserum against the pET30a-RLN3 antigen. When the titer was greater than 1:50,000, the final blood collection was conducted to prepare an antiserum, and the antiserum was purified.

(5) Titer Detection by Indirect ELISA

1) Antigen coating: The pET30a-pET30a-RLN3 antigen was dissolved in a 0.05 mol/L carbonate solution at 6 μg/mL and then added to a microplate at 100 μL/well, and the microplate was incubated at 4° C. overnight.

2) Microplate washing: The microplate was washed three times with 0.05% Tween-20-containing PBS for 3 min each time.

3) Blocking: 150 μL of a 5% skimmed milk powder was added to each well to block at 37° C. for 60 min.

4) Microplate washing: The microplate was washed three times with 0.05% Tween-20-containing PBS for 3 min each time.

5) Primary antibody addition: Serum of the rabbit was diluted at 1:1,000, then serially diluted, and added to the microplate, and the microplate was incubated at 37° C. for 1 h.
6) Microplate washing: The microplate was washed three times with 0.05% Tween-20-containing PBS for 3 min each time.
7) Secondary antibody addition: Goat anti-rabbit IgG-HRP was diluted at 1:8,000 and added to the microplate, and the microplate was incubated at 37° C. for 45 min.
8) Microplate washing: The microplate was washed five times with 0.05% Tween-20-containing PBS for 3 min each time.
9) Color development: A substrate solution (TMB) was added at 100 μL/well to allow a reaction for about 15 min, and finally 2 mol/L sulfuric acid was added at 100 μL/well to stop the reaction.
10) OD value determination: An OD value at 450 nm was determined by a microplate reader. Determination results were shown in Table 4.

TABLE 4

| OD values at 450 nm | | |
| --- | --- | --- |
| No. | Antibody dilution factor | $OD_{450}$ |
| 1 | 1000 | 1.493 |
| 2 | 2000 | 1.361 |
| 3 | 4000 | 1.185 |
| 4 | 8000 | 1.004 |
| 5 | 16000 | 0.704 |
| 6 | 32000 | 0.345 |
| 7 | 64000 | 0.239 |
| 8 | 128000 | 0.152 |
| 9 | Blank | 0.073 |
| — | Tter | >128,000 |

A starting dilution ratio is 1:1000, and a titer refers to the maximum dilution ratio when a sample OD/blank≥2.

(6) Antibody Purification
  1) Conjugation: 2 mg of the pET30a-pET30a-RLN3 antigen was conjugated to 1.5 mL of a CNBr-activated agarose resin.
  2) Incubation: 10 mL of an antiserum and 1.5 mL of a CNBr-activated agarose resin were incubated at 4° C. overnight.
  3) Pre-elution: 5 mL of a pre-elution buffer was added to elute heteroproteins binding to the CNBr-activated agarose resin.
  4) Elution: 1 mL of an elution buffer was added, and an eluate was collected using an EP tube with 50 μL of a neutralization solution, which was repeated 10 times at an interval of 90 s.
  5) Concentration determination: The collected antibody was determined with a microspectrophotometer to have a concentration of 0.95 mg/mL.

It was determined by ELISA that a titer of the anti-RLN30 antibody was 128 K, indicating the successful preparation of the anti-RLN3 polyclonal antibody.

Example 4

A method for detecting giant panda RLN3 was specifically as follows:
1. Construction of an Assay Kit
  (1) The anti-RLN3 polyclonal antibody obtained in Example 3 was labeled with biotin specifically as follows:
    a. A polyclonal antibody to be biotinylated was subjected to adequate dialysis with a 0.1 mol/L sodium bicarbonate buffer (pH 8.0) to obtain a target antibody solution.
    b. 1 mg of N-hydroxysuccinimide ester-biotin (NHSB) was dissolved with 1 mL of DMF to obtain an NHSB solution.
    c. 150 g of the NHSB solution (including 150 g of NHSB) was added to 1 mg of the target antibody solution to obtain a mixed solution.
    d. The mixed solution was continuously stirred at room temperature and incubated for 2 h to 4 h.
    e. 10 μL of 1 mol/L $NH_4CL$ was added, and stirring was conducted for 10 min at room temperature.
    f. PBS was fully dialyzed at 4° C. to remove free biotin.
  (2) A microplate with a high binding rate and a low background was coated with the anti-giant panda RLN3 monoclonal antibody as a "primary antibody". A standard antibody coating concentration and preparation method was adopted (10 μg/mL, detailed in Harlow and Lane, Antibodies, a Laboratory Manual, Cold Spring Harbor, NY, p139, 1988).
  (3) A detection signal was amplified with a biotin-labeled anti-RLN3 polyclonal antibody as a "secondary antibody" and then with a commercial multi-chain streptoavidin-HRP complex.
  (4) The pET30a-pET30a-RLN3 recombinant protein prokaryotically expressed in Example 3 was adopted as a standard for the detection method.
  (5) Finally, the assay kit was constructed in combination with conventional components in the assay kit, including: a sample buffer, a wash buffer, a chromogen substrate solution (TMB solution), a chromogen stop solution (1 M sulfuric acid solution), or the like.

A detection principle of the kit was as follows:

The anti-giant panda RLN3 monoclonal antibody was coated on a 96-well microplate, and a soluble residual protein of RLN3 metabolism in urine bound to the anti-giant panda RLN3 monoclonal antibody. Then, the biotin-labeled anti-RLN3 polyclonal antibody underwent sandwich binding to the residual RLN3 protein binding to the anti-giant panda RLN3 monoclonal antibody. The streptoavidin-RP complex bound to the biotin-labeled anti-RLN3 polyclonal antibody, and finally a chromogen substrate (TMB) was catalyzed by HRP for color development. A concentration of RLN3 in a test sample was determined according to a standard curve.

2. Detection with the Constructed Kit

1) During the detection, giant panda urine was added at 0.05 mL/well to a microplate coated with the anti-giant panda RLN3 monoclonal antibody. A sample diluent was added to prepare pET30a-RLN3 recombinant protein standards at 0 ng/mL to 5,000 ng/mL (0, 0.073, 0.146, 0.291, 0.583, 1.166, 2.33, 4.66, 9.325, 18.75, 37.5, 75, 150, and 300), with 13 standard points in total. The microplate was incubated at 37° C. for 30 min.
2) The microplate was washed 5 times with a washing solution.
3) An anti-RLN polyclonal antibody-biotin complex diluted with the sample diluent at 1:1,000 was added at 0.05 mL/well.
4) The microplate was incubated at 37° C. for 30 min.
5) The microplate was washed 5 times with a washing solution.

6) A strepoavidin-RP complex diluted with the sample diluent at 1:1,000 was added at 0.05 mL/well, and the microplate was incubated at 37° C. for 30 min.
7) The microplate was washed 5 times with a washing solution.
8) A TMB working solution was added at 0.1 mL/well. The microplate was incubated at room temperature for 10 min to 15 min.
9) 1 M sulfuric acid was added at 0.1 mL/well to stop a chromogenic reaction.
10) An optical density of each standard well at 450 nm was read on a microplate reader, and then a content of TSH in a sample was calculated according to a standard curve.

Figure 3:
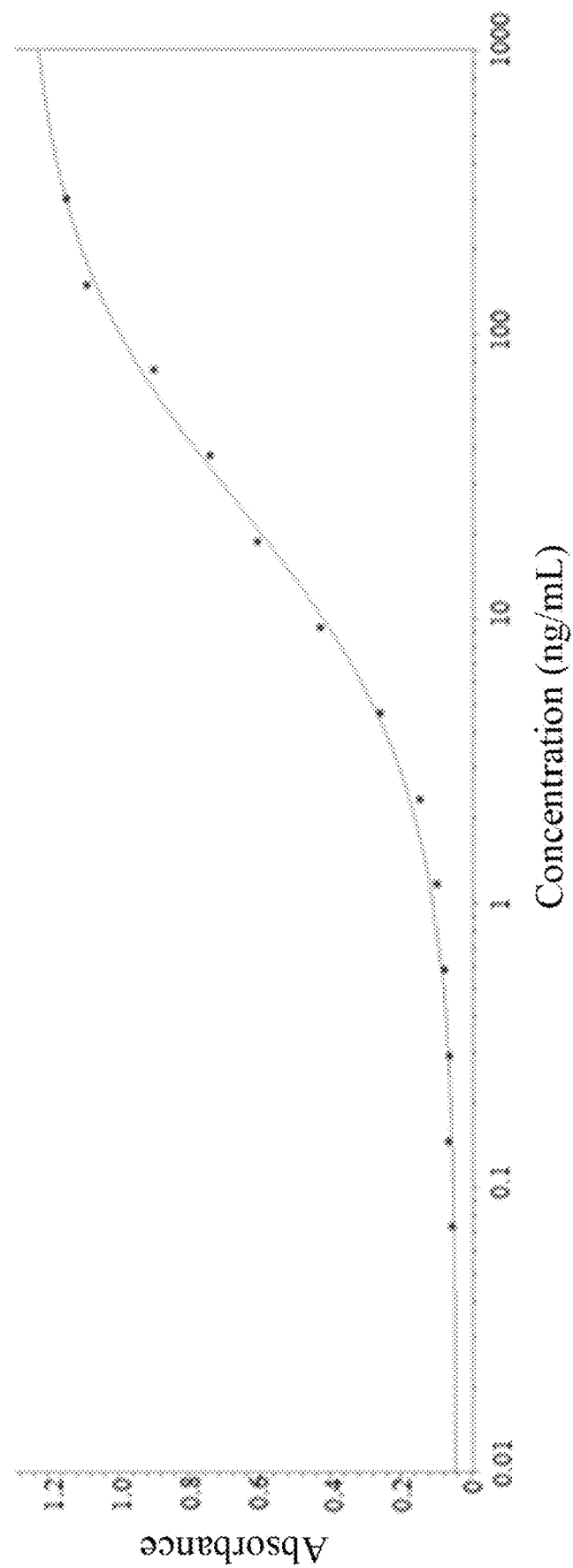
FIG. 3 shows a standard curve of an RLN3 assay kit.

The plotted standard curve was shown in FIG. 3.

Example 5

Figure 4:
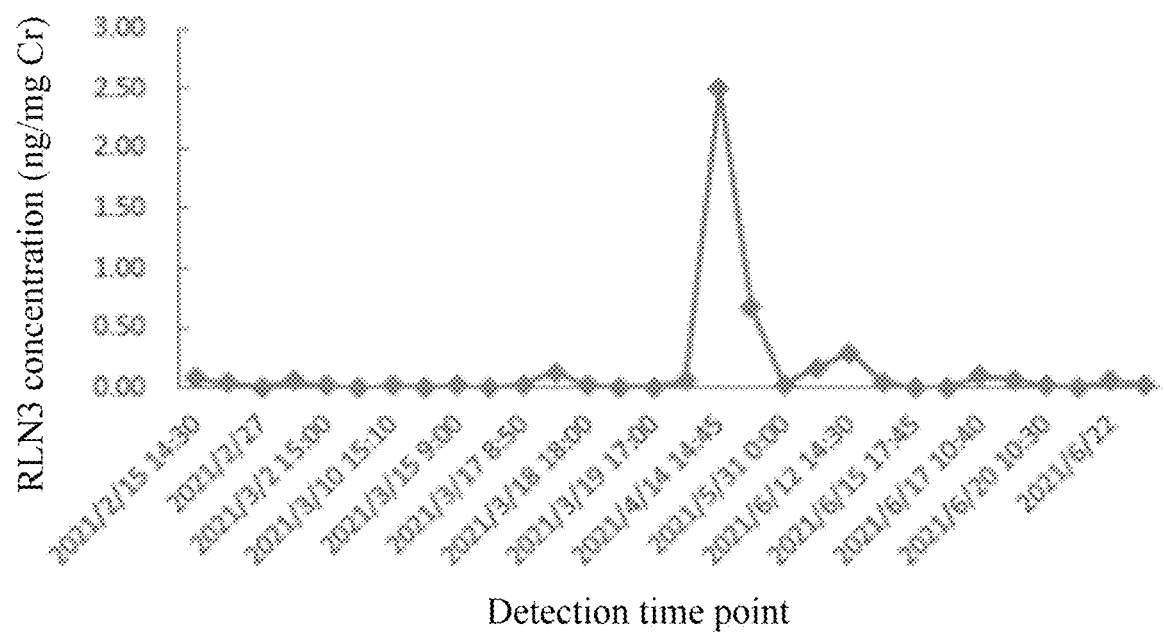
FIG. 4 shows a change in RLN3 detection.

Based on the RLN3 assay kit constructed in Example 4 of the present application, urine RLN3 can be detected and corrected with creatinine to allow the timely monitoring of an RLN3 change (as shown in FIG. 4, an RLN3 concentration is corrected with a creatinine concentration in urine, and is in a unit of ng/mg Cr).

What is claimed is:

1. An enzyme-linked immunosorbent assay (ELISA) method for giant panda relaxin-3 (RLN3), comprising:
   conducting ELISA with an anti-giant panda RLN3 monoclonal antibody as a coating antibody and an anti-RLN3 polyclonal antibody as a labeling antibody, wherein
   the anti-giant panda RLN3 monoclonal antibody is secreted by a hybridoma cell line RLN-3 and the hybridoma cell line RLN-3 is deposited in China Center for Type Culture Collection (CCTCC) of Wuhan University, Wuhan, China on Jan. 7, 2021, with an accession number of CCTCC NO: C202129; and
   the anti-giant panda RLN3 monoclonal antibody comprises a heavy-chain variable region with the amino acid sequence shown in SEQ ID NO: 1 and a light-chain variable region with the amino acid sequence shown in SEQ ID NO: 2.

2. The ELISA method for the giant panda RLN3 according to claim 1, wherein the anti-RLN3 polyclonal antibody is produced by a rabbit stimulated with the immunogen shown in SEQ ID NO: 6.

3. The ELISA method for the giant panda RLN3 according to claim 1, wherein during the ELISA, the anti-RLN3 polyclonal antibody is configured to be labeled with a biotin.

4. An anti-giant panda RLN3 monoclonal antibody, comprising a heavy-chain variable region with the amino acid sequence shown in SEQ ID NO: 1 and a light-chain variable region with the amino acid sequence shown in SEQ ID NO: 2.

5. A hybridoma cell line RLN-3 secreting the anti-giant panda RLN3 monoclonal antibody according to claim 4, wherein the hybridoma cell line RLN-3 is deposited in China Center for Type Culture Collection (CCTCC) of Wuhan University, Wuhan, China on Jan. 7, 2021, with an accession number of CCTCC NO: C202129.

6. The ELISA method for the giant panda RLN3 according to claim 2, wherein during the ELISA, the anti-RLN3 polyclonal antibody is configured to be labeled with a biotin.

* * * * *